(12) United States Patent
Han (10) Patent No.: US 12,014,810 B2
(45) Date of Patent: Jun. 18, 2024

(54) SYSTEM AND METHOD FOR IMPROVING COGNITIVE ABILITY AND COMPUTER PROGRAM FOR THE SAME

(71) Applicant: ROWAN Inc., Seoul (KR)

(72) Inventor: Seung Hyun Han, Goyang-si (KR)

(73) Assignee: ROWAN INC., Seoul (KR)

( * ) Notice: Subject to any disclaimer, the term of this patent is extended or adjusted under 35 U.S.C. 154(b) by 414 days.

(21) Appl. No.: 17/434,549

(22) PCT Filed: Mar. 4, 2021

(86) PCT No.: PCT/KR2021/002695
§ 371 (c)(1),
(2) Date: Aug. 27, 2021

(87) PCT Pub. No.: WO2022/177046
PCT Pub. Date: Aug. 25, 2022

(65) Prior Publication Data
US 2023/0116521 A1  Apr. 13, 2023

(30) Foreign Application Priority Data

Feb. 17, 2021 (KR) .......................... 10-2021-0020809

(51) Int. Cl.
*G16H 20/70* (2018.01)
*G16H 50/20* (2018.01)

(52) U.S. Cl.
CPC ............. *G16H 20/70* (2018.01); *G16H 50/20* (2018.01)

(58) Field of Classification Search
None
See application file for complete search history.

(56) References Cited

U.S. PATENT DOCUMENTS 7,070,563 B2 * 7/2006 Buschke ................ G16H 50/70
                                                            600/300
8,078,253 B2 * 12/2011 Teicher .................. A61B 5/168
                                                            600/407
(Continued)

FOREIGN PATENT DOCUMENTS

| KR | 10-1295187 B1 | 8/2013 |
| KR | 10-1295187 B1 | 9/2013 |
| KR | 10-2018-0041089 A | 4/2018 |

OTHER PUBLICATIONS

Koo et al., "Mobile Technology for Cognitive Assessment of Older Adults: a Scoping Review", 2019, Innovation in Aging, VOl 3 No. 1, 1-14 (Year: 2019).*

*Primary Examiner* — Evangeline Barr
*Assistant Examiner* — Anne-Marie K Alderson
(74) *Attorney, Agent, or Firm* — NKL Law; Byungwoong Park (57) ABSTRACT

A system for improving cognitive ability includes a content providing module configured to provide a cognitive ability improving content; an input module configured to receive learning data of the user for the cognitive ability improving content; an analyzing module configured to calculate performance information of each of a plurality of cognitive areas based on the learning data; and a machine learning module configured to store a learning result by machine learning using a preset training data set and determine a characteristic of a cognitive ability improving content to be provided to a user by using the performance information of each of the plurality of cognitive areas and the learning result. According to the system for improving cognitive ability, it is possible to provide a content in the form of a comprehensive program including multi-area intervention important for dementia prevention and perform a custom- (Continued)

ized dementia prevention function by reflecting individual characteristics.

9 Claims, 7 Drawing Sheets

(56) References Cited

U.S. PATENT DOCUMENTS

| | | | |
|---|---|---|---|
| 11,386,803 B1* | 7/2022 | Moreno | G16H 20/70 |
| 2015/0010890 A1* | 1/2015 | Kang | G16H 20/40 |
| | | | 434/236 |
| 2016/0262680 A1* | 9/2016 | Martucci | A61B 5/4088 |
| 2020/0302296 A1 | 9/2020 | Miller | |
| 2021/0005305 A1* | 1/2021 | Lee | A61B 5/4836 |

* cited by examiner

SYSTEM AND METHOD FOR IMPROVING COGNITIVE ABILITY AND COMPUTER PROGRAM FOR THE SAME

FIELD

Embodiments relate to a system and method for improving cognitive ability and a computer program for the same. More specifically, the embodiments relates to a technology associated with a system for improving cognitive ability, which performs a customized dementia prevention function by reflecting individual characteristics through a comprehensive program including multi-area intervention important for dementia prevention and may be used by multiple users since it may be implemented not only in an institutional type where the system is used by a user visiting an institution and but also in an at-home type where the system is used at home.

BACKGROUND

As the average lifespan increases due to the development of medicine, an aging population is progressing around the world. In the case of Korea, in 2000, the proportion of the population aged 65 and over was 7.2% of the total population, thereby entering an aging society, and in 2017, the proportion of the elderly population exceeded 14%, thereby entering an aged society. By 2030, the proportion of the elderly population in Korea is predicted to reach 24.3%, so that Korea will become a super-aged society.

Due to such rapid aging, the dementia population is rapidly increasing. The global dementia population reached about 35.6 million as of 2010, and is expected to substantially triple to 115.4 million by 2050. In Korea, the prevalence of dementia by year is 9.08% in 2012, which increases to 9.74% in 2020, 9.61% in 2030, 11.21% in 2040, and 13.17% in 2050, and it is predicted that the number of dementia population will exceed 1 million in 2027 and reach 2.12 million in 2050.

As the dementia population rapidly increases, the cost of treatment and management of dementia is also increasing. The social cost for dementia is estimated to exceed the combined cost of all three diseases: cancer, heart disease and stroke. In Korea, the total annual medical cost for dementia was KRW 810 billion as of 2010, which is the second highest among geriatric diseases, and the annual dementia treatment cost per capita was KRW 3.1 million, which is the highest among the five major chronic diseases. In addition, the total national dementia cost in Korea was KRW 8.7 trillion per year, which is estimated to be doubled every 10 years.

In order to reduce the social and economic burden caused by the rapidly increasing dementia, it is necessary to delay the onset of dementia through active treatment by early detection of high-risk groups of dementia. As a prior art for this, Korean Patent No. 10-1295187 discloses a brain function improvement system that performs a dementia prevention function by granting an achievement level to a user according to the score obtained by a feedback of the user delivered for a selected content, and its operation method.

However, the conventional cognitive interventional treatment for dementia prevention and treatment requires a user to visit a hospital or other institution and should be conducted under the supervision of an expert, so in most cases, a high treatment cost of KRW 50,000 to 120,000 must be paid at a time. In addition, although a cognitive interventional treatment program using a computing device has been developed, there is a limit in that it is difficult for general users to use the program due to high cost of KRW 50 million per device.

Related Technology: (Patent Document 1) Korean Patent No. 10-1295187

SUMMARY

In an aspect of the present disclosure, there is provided a system for improving cognitive ability, which may be implemented in the form of a comprehensive program including multi-area intervention important for dementia prevention to perform a customized dementia prevention function by reflecting individual characteristics and may be implemented not only in an institutional type where the system is used by a user visiting an institution and but also in an at-home type where users are managed by communication through a network.

A system for improving cognitive ability according to an embodiment comprises a content providing module configured to provide a cognitive ability improving content to a user; an input module configured to receive learning data of the user for the cognitive ability improving content; an analyzing module configured to calculate performance information of each of a plurality of cognitive areas based on the learning data; and a machine learning module configured to store a learning result by machine learning using a preset training data set and determine a characteristic of a cognitive ability improving content to be provided to the user by using the performance information of each of the plurality of cognitive areas and the learning result.

In an embodiment, the input module may be further configured to receive the training data set, and the input module may comprise a data labeling unit configured to label the training data set by using a customized content preset for data included in the training data and provide the labeled data to the machine learning module.

In an embodiment, the analyzing module may be further configured to determine the performance information based on at least one of a recognition score of each of the plurality of cognitive areas, a consumed time of each of the plurality of cognitive areas, a progress rate of each of the plurality of cognitive areas and a participation rate of each of the plurality of cognitive areas.

In an embodiment, the input module may be further configured to receive personal information of the user. At this time, the analyzing module may be further configured to determine a reference value for deriving the performance information from at least one of the recognition score, the consumed time, the progress rate and the participation rate by using the personal information of the user.

In an embodiment, the machine learning module may include a machine learning model learning unit configured to generate the learning result by performing machine learning using the training data set; and a machine learning model determining unit configured to determine a characteristic of the cognitive ability improving content corresponding to the performance information of each of the plurality of cognitive areas by using the learning result.

A method for improving cognitive ability according to an embodiment comprises: by a system for improving cognitive ability, generating a learning result by machine learning using a preset training data set; storing the learning result in the system for improving cognitive ability; by the system for improving cognitive ability, providing a cognitive ability improving content to a user; by the system for improving cognitive ability, receiving learning data of the user for the cognitive ability improving content; by the system for improving cognitive ability, calculating performance information of each of a plurality of cognitive areas based on the learning data; and by the system for improving cognitive ability, determining a characteristic of a cognitive ability improving content to be provided to the user by using the performance information of each of the plurality of cognitive areas and the learning result.

In an embodiment, the step of generating a learning result may include: by the system for improving cognitive ability, receiving the training data set; and by the system for improving cognitive ability, labeling the training data set by using a customized content preset for data included in the training data set.

In an embodiment, the step of calculating performance information may include: by the system for improving cognitive ability, determining the performance information based on at least one of a recognition score of each of the plurality of cognitive areas, a consumed time of each of the plurality of cognitive areas, a progress rate of each of the plurality of cognitive areas and a participation rate of each of the plurality of cognitive areas.

The method for improving cognitive ability according to an embodiment may further comprise: before the step of calculating performance information, by the system for improving cognitive ability, receiving personal information of the user; and by the system for improving cognitive ability, determining a reference value for deriving the performance information from at least one of the recognition score, the consumed time, the progress rate and the participation rate by using the personal information of the user.

A computer program according to an embodiment is stored in a computer-readable recording medium and is coupled to hardware to execute the method for improving cognitive ability according to the former embodiments.

According to the system and method for improving cognitive ability and according to an aspect of the present disclosure, it is possible to perform customized dementia prevention by reflecting individual characteristics through a comprehensive program including multi-area intervention important for dementia prevention, such as cognition, motivation, blood vessels, exercise and nutrition.

In addition, the system and method for improving cognitive ability according to an aspect of the present disclosure may be implemented not only in an institution-type where the system is used by a user visiting senior welfare centers or dementia relief centers, but also through an at-home program in which users are managed through a network to prevent dementia, so even the elderly who have difficulty in visiting an institution may use the system through the Internet, thereby allowing more users to have a benefit from the dementia prevention program than before.

Further, if the system and method for improving cognitive ability according to an aspect of the present disclosure is used, by configuring the program to be customized for users to participate continuously, there is an advantage of correcting lifestyles of the users for dementia prevention and strengthening the motivation of the users to consistently practice activities based on accurate knowledge.

DETAILED DESCRIPTION OF THE EMBODIMENTS

Hereinafter, embodiments of the present disclosure will be described in detail with reference to the drawings.

Figure 1:
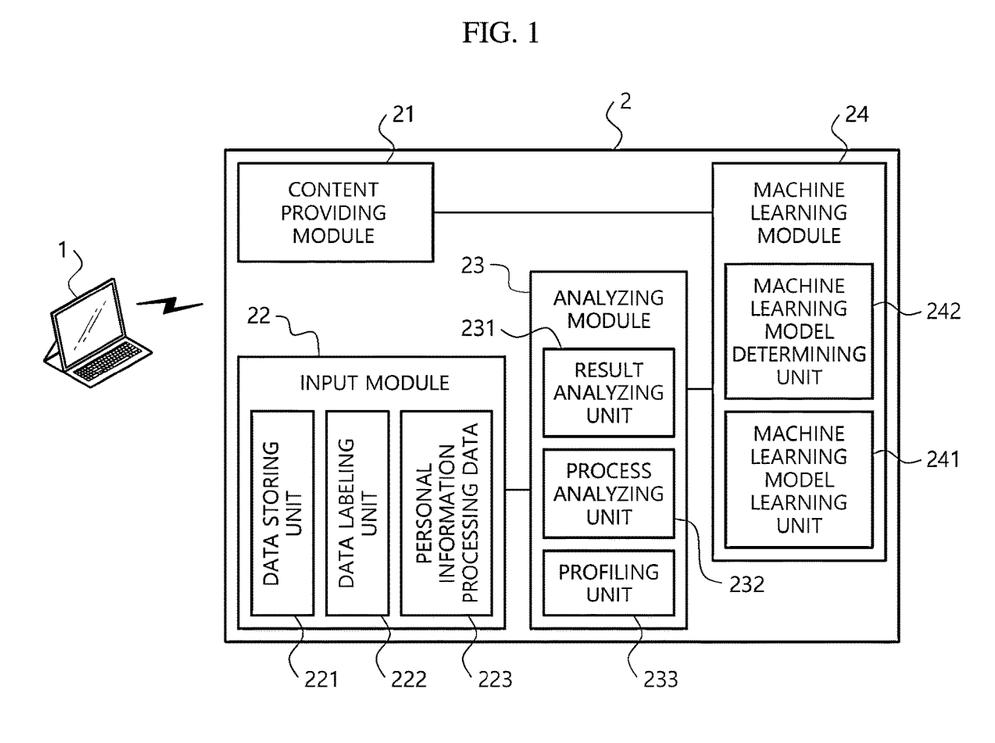
FIG. 1 is a schematic block diagram showing a system for improving cognitive ability according to an embodiment.

FIG. 1 is a schematic block diagram showing a system for improving cognitive ability according to an embodiment.

Referring to FIG. 1, a system 2 for improving cognitive ability according to this embodiment includes a content providing module 21, an input module 22, an analyzing module 23 and a machine learning module 24. In addition, each module 21 to 24 may include one or a plurality of functional units.

The system 2 for improving cognitive ability and each module 21 to 24 or unit included therein according to embodiments may have aspects that are entirely hardware or partially hardware and partially software. For example, each module 21 to 24 or unit of the system 2 for improving cognitive ability may collectively refer to hardware and related software for processing data of a specific format and content and/or sending and receiving data in an electronic communication method. In this specification, terms such as "unit," "module," "device," "terminal," "server," or "system," are intended to refer to a combination of hardware and software driven by the hardware. For example, the hardware may be a data processing device including a CPU or other processor. In addition, the software driven by hardware may refer to a running process, an object, an executable file, a thread of execution, a program, and the like.

In addition, each element constituting the system 2 for improving cognitive ability is not necessarily intended to refer to separates device physically distinguished from each other. That is, the content providing module 21, the input module 22, the analyzing module 23 and the machine learning module 24 of FIG. 1 are merely functionally distinguished according to the operation performed by the hardware constituting the system 2 for improving cognitive ability, and it is not always necessary that each unit should be provided independently from each other. Of course, depending on embodiments, it is also possible that one or more of the content providing module 21, the input module 22, the analyzing module 23 and the machine learning module 24 are implemented as separate devices that are physically distinguished from each other.

The content providing module 21 is configured to provide a user with a content for improving cognitive ability. For example, the content providing module 21 may be a part for transmitting a content to a user device 1 so that the content may be presented to the user using a display means, a sound output means, or the like provided to the user device 1. For the above operation, the system 2 for improving cognitive ability may communicate with the user device 1 through a wired and/or wireless network. In this specification, a communication method through a wired and/or wireless network may include any communication method capable of networking between objects and is not limited to wired communication, wireless communication, 3G, 4G, or other methods.

Although the user device 1 is shown in the form of a tablet computer in FIG. 1, this is an example, and the user device 1 may be configured as any mobile computing device such as a smartphone, or any computing device such as a notebook computer, a personal computer (PC), etc.

In an embodiment, the system 2 for improving cognitive ability may at least partially perform a function of an application server that enables to execute a function of an application by communicating with an application (or, an app) executed on the user device 1. In addition, the system 2 for improving cognitive ability may also at least partially perform a function of a web server that provides a predetermined web page accessible through a web browser running on the user device 1, or the like.

However, this is an example, and in another embodiment, the system 2 for improving cognitive ability may be configured in the form of a device used by the user in itself, and in this case, the user may use a content directly through the system 2 for improving cognitive ability, so the user device 1 shown in FIG. 1 may be omitted.

In embodiments of the present disclosure, a cognitive ability improving content presented through the content providing module 21 may be related to a plurality of cognitive areas. In this specification, the plurality of cognitive areas refer to multifaceted fields for inducing activities to improve the cognitive ability of the user from different viewpoints in order to improve the cognitive ability by preventing or slowing down the decline in cognitive ability due to dementia, etc.

For example, in an embodiment, the system 2 for improving cognitive ability may classify contents that needs to be managed for improving cognitive ability into five cognitive areas: vascular disease management, cognitive training, exercise, nutrition management, and motivation enhancement. At this time, the cognitive ability improving content provided by the system 2 for improving cognitive ability aims to improve the ability of one or a plurality of cognitive areas among the five cognitive areas described above, and may be developed with the goal of strengthening a specific cognitive area. In this specification, this is referred to as a characteristic of the cognitive ability improving content. For example, the cognitive ability improving content may be in the form of a game aimed at enhancing ability in a specific field.

The input module 22 is configured to receive, from the user device 1, learning data of a user for a content provided to the user through the content providing module 21. Alternatively, if the system 2 for improving cognitive ability is implemented in the form of a user device such as a personal computer of the user, the input module 22 may receive the learning data through an input means (not shown) such as a keyboard or a touch screen.

The analyzing module 23 is configured to calculate performance information of each of the plurality of cognitive areas by analyzing the learning data input to the input module 22. For example, the analyzing module 23 may determine the performance information based on a recognition score for the content (e.g., game) of each cognitive area, a consumed time for the content of each area, a progress rate of each area and/or a participation rate of each area.

To this end, in an embodiment, the analyzing module 23 may include a result analyzing unit 231 for analyzing a recognition score, which is a learning result of the user for each area, and/or a process analyzing unit 232 for analyzing information on the time taken for achieving the goal of the content of each area and a consumed time such as a response time of the user for the content.

In addition, in an embodiment, the analyzing module 23 further includes a profiling unit 233. In this embodiment, the user may input his/her personal information, for example gender, age, living environment (number of household members, etc.), and medical history such as past dementia diagnosis through the input module 22. The profiling unit 233 is configured to determine a reference value for deriving performance information from the learning data, based on the personal information. At this time, the reference value may refer to information about an area for converting the recognition score or the consumed time into a performance value, weight information to be applied to the recognition score or the consumed time, or an adjustment value in any other way to give an effect to the performance value by gender/age/living environment/medical history of the user.

The machine learning module 24 functions to store a learning result by machine learning using a training data set input in advance, and determine a characteristic of a user customized content by applying the learning result of machine learning to the performance information obtained by the analyzing module 23.

For the above operation, the machine learning module 240 may include a machine learning model learning unit 241 for performing machine learning using the training data set, and a machine learning model determining unit 242 for determining a customized content for the performance information of the user based on the learning result.

In an embodiment, the input module 22 may further perform the function of receiving the training data set and inputting the training data set to the machine learning model learning unit 241 for machine learning. In this case, the input module 22 may include a data storing unit 221 and a data labeling unit 222. The data labeling unit 222 is suitable for improving the cognitive ability of the user who has provided the corresponding data with respect to the data included in the training data set, and the data labeling unit 222 may label the data of the training data set by using customized content information (i.e., a correct answer) determined by experts or clinical results and provide the labeled data to the machine learning model learning unit 241.

Also, the input module 22 may further include a personal information processing unit 223. The personal information processing unit 223 may perform masking on the personal information so that sensitive personal information of each user is not exposed when the machine learning model learning unit 241 performs learning using the training data set. At this time, the masking may refer to deleting sensitive information itself from the training data set. Alternatively, even if the corresponding information is not deleted, the masking may refer to dividing, combining or reconstructing data so that it is impossible to match data records with a person who has provided the data records.

The machine learning model determining unit 242 of the machine learning module 24 may determine the type of user corresponding to the performance information of the user based on data previously accumulated by the machine learning model learning unit 241, and determine the characteristic of a customized content suitable for the user. For example, determining the type of the user may mean classifying or clustering users based on a pattern of performance shown by the user in a plurality of cognitive areas, and the machine learning model determining unit 242 may determine a customized content suitable for improving the cognitive ability of the corresponding user classification or cluster by using the type.

Figure 2:
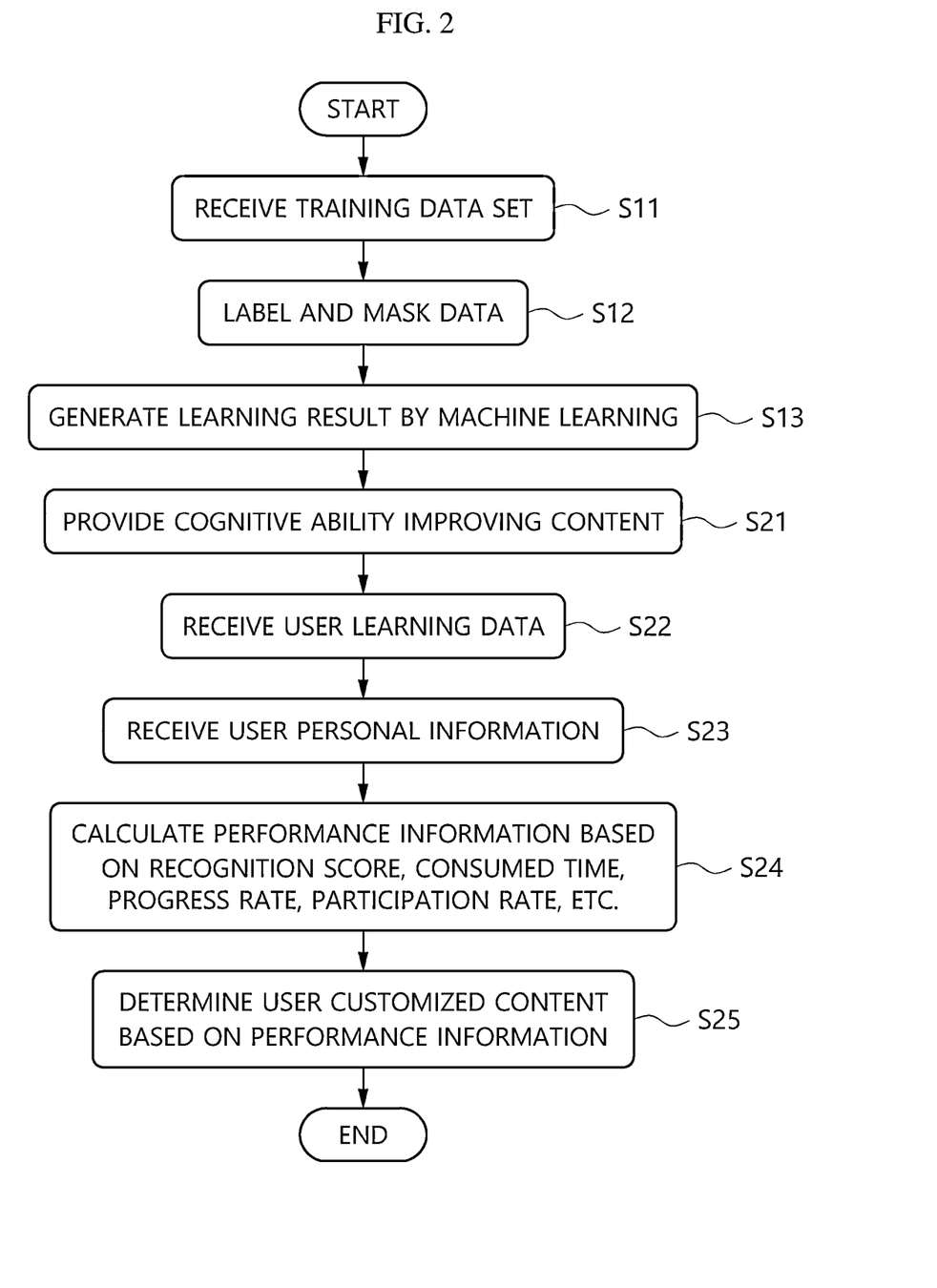
FIG. 2 is a flowchart showing each step of a method for improving cognitive ability according to an embodiment.

FIG. 2 is a flowchart showing each step of a method for improving cognitive ability according to an embodiment. For convenience of explanation, a method for improving cognitive ability according to this embodiment will be described with reference to FIGS. 1 and 2.

Referring to FIG. 2, first, as a machine learning-based learning process, the input module 22 of the system 2 for improving cognitive ability may receive a training data set (S11). The training data set may be input or transmitted to the input module 22 from a user device of a manager, or may be received from an external server (not shown).

As a pre-processing process for performing machine learning using the training data set, the data labeling unit 222 of the input module 22 may label the data using customized content information determined based on experts or clinical trials by each data of the training data set (S12). In addition, the personal information processing unit 223 of the input module 22 may remove sensitive information from the data of the training data set or perform masking so that sensitive information is not associated with an individual data provider (S12).

The machine learning module 24 of the system 2 for improving cognitive ability may receive the data that is completely labeled and masked, and use the data to generate a learning result for determining a customized content from the learning data (S13). For example, the learning result may be used to determine the type of user based on the pattern of the learning data and to determine characteristics of a content suitable to be applied to a user of the corresponding type, for example, the type and number of cognitive areas corresponding to the content.

The learning process S11 to S13 by machine learning as described above may be performed by the machine learning model learning unit 241 of the machine learning module 24. However, in another embodiment, the machine learning module 24 may receive an algorithm, a parameter, or the like corresponding to the machine learning result from an external device or server and operate based thereon. In this case, the learning process S11 to S13 described above may be omitted.

In order to provide the customized content to a target user based on the learning result by machine learning, first, the content providing module 21 of the system 2 for improving cognitive ability may provide the user with a cognitive ability improving content having a characteristic for each of a plurality of cognitive areas (S21).

Next, the input module 22 of the system 2 for improving cognitive ability may receive the learning data of the user for the provided content (S22). For example, the learning data may include a recognition score, which is achieved as the user solves a task provided through the content in the form of, for example, a game, a time consumed by the user to achieve the task, and a progress rate and a participation rate of the user for a series of tasks in the content.

In an embodiment, the input module 22 may further receive personal information of the user participating in the content at the same time as receiving the learning data or before or after receiving the learning data (S23). For example, the personal information may include information such as gender/age/residence environment/medical history of the user, but is not limited thereto.

The analyzing module 23 of the system 2 for improving cognitive ability may derive performance information suitable for determining the type of user indicated by the learning data from the learning data of the user (S24). For example, the performance information may refer to a recognition score, a consumed time, a progress rate, a participation rate, etc. achieved by the user for the content, or may be a performance value configured from this information according to a predetermined standard (grade, threshold, weight, etc.).

The machine learning module 24 of the system 2 for improving cognitive ability may determine a user customized content based on the performance information derived by the analyzing module 23 (S25). This may mean determining a characteristic (type, difficulty, time limit, etc.) of the cognitive ability improving content suitable to be presented to the corresponding user next, based on the type of user determined through the machine learning model, and will be described in detail later.

Figure 3:
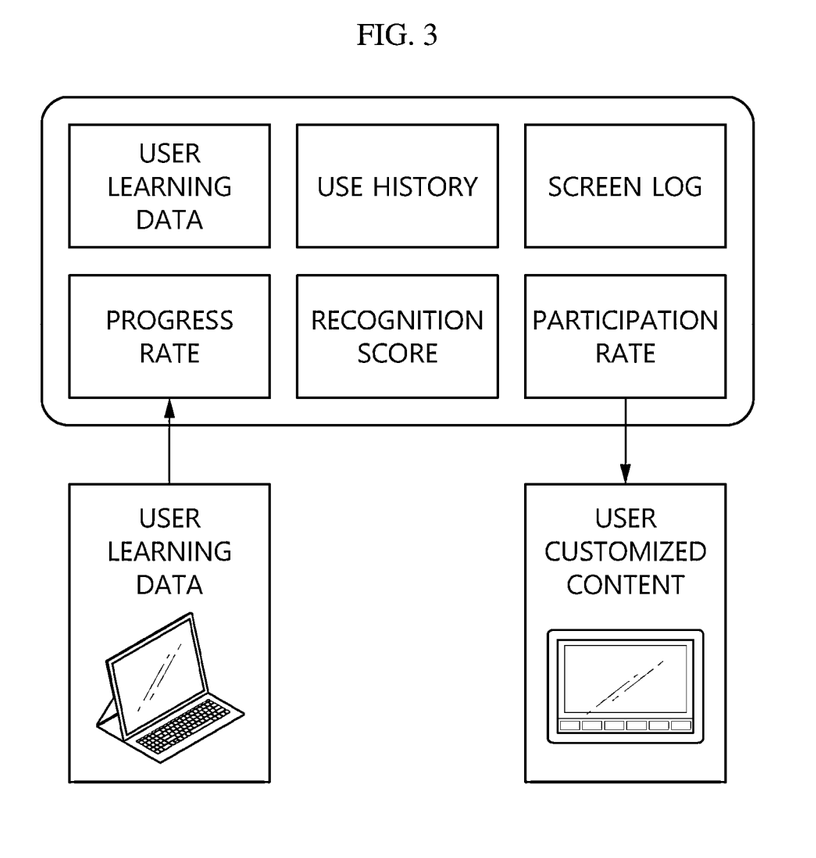
FIG. 3 is a concept view for illustrating a data processing step by the method for improving cognitive ability according to an embodiment.

FIG. 3 is a concept view for illustrating a data processing step by the method for improving cognitive ability according to an embodiment.

Referring to FIG. 3, in the method for improving cognitive ability according to embodiments of the present disclosure, information such as a user history, a progress rate, a recognition score and/or a participation rate may be derived from the learning data of the user, and a customized content to be provided to the user may be determined by using the information as performance information.

In this specification, the recognition score refers to a score achieved by the user on a task provided through a content based on multi-area intervention including a plurality of cognitive areas. For example, if the cognitive ability improving content is a content having five cognitive areas: vascular disease management, cognitive training, exercise, nutrition management and motivation enhancement, the recognition score may be a data set including scores for areas as a data record like {30, 40, 10, 5, 80}.

FIGS. 4A to 4F are exemplary images showing a screen of a content provided by the system for improving cognitive ability according to an embodiment, and show a screen of a content corresponding to cognitive training among the five cognitive areas for vascular disease management, cognitive training, exercise, nutrition management and motivation enhancement.

Figure 4A:
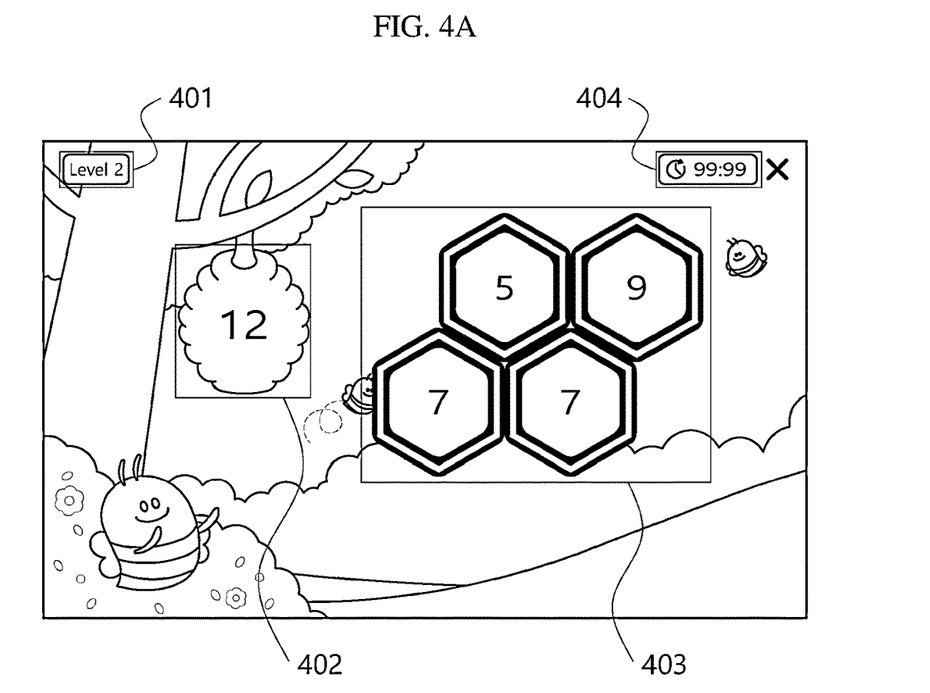
FIG. 4A is an exemplary image showing a screen of a content provided by the system for improving cognitive ability according to an embodiment.

Referring to FIG. 4A, a user participating in the cognitive training may see a question image 402 presented on the screen, and select a plurality of panels for deriving a sum equal to the number displayed in the question image 402 among a plurality of number panels included in an answer image 403. At this time, the content may include tasks for each difficulty corresponding to a plurality of difficulties as shown in the level image 401 on the screen, and the content may be configured so that the difficulty of a presented task gradually increases as the task of a lower level is achieved. In addition, as displayed as a timer image 404, the time consumed by the user to solve the task may be recorded by the system for improving cognitive ability.

Figure 4B:
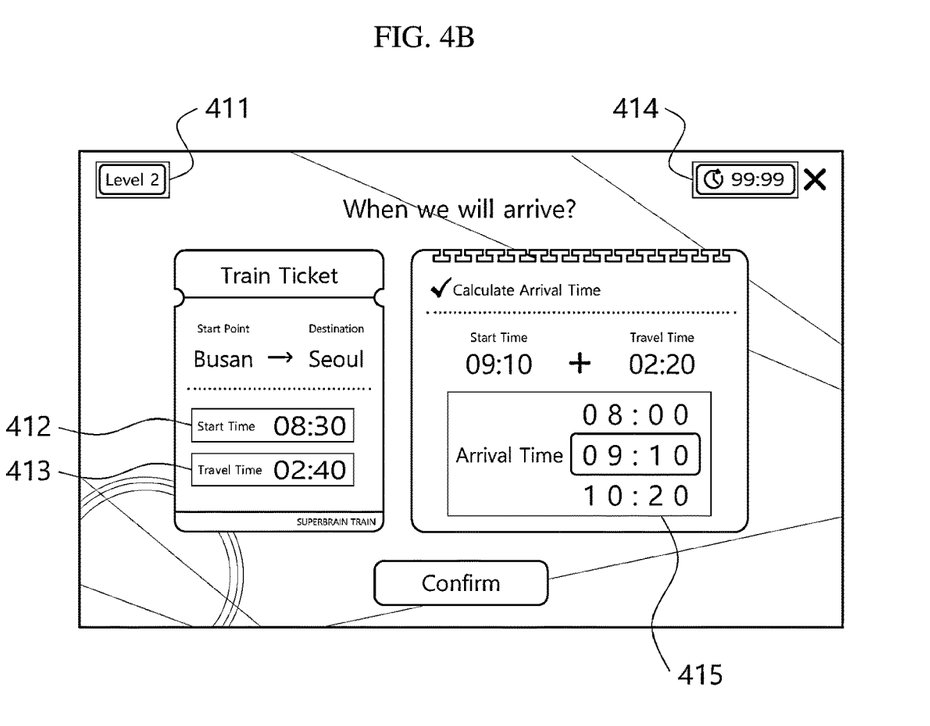
FIG. 4B is an exemplary image showing a screen of a content provided by the system for improving cognitive ability according to an embodiment.

Referring to FIG. 4B, as an example of another form of cognitive training, the user may perform a task of checking a departure time and a travel time from question images 412, 413 presented as a task, calculating an arrival time by adding the travel time to the departure time, and selecting the calculated time as an arrival time using an answer image 415. Like the content screen illustrated in FIG. 4A, in the case of this content, a level image 411 indicating the difficulty of the task and/or a timer image 414 indicating a consumed time may be further displayed on the screen.

Figure 4C:
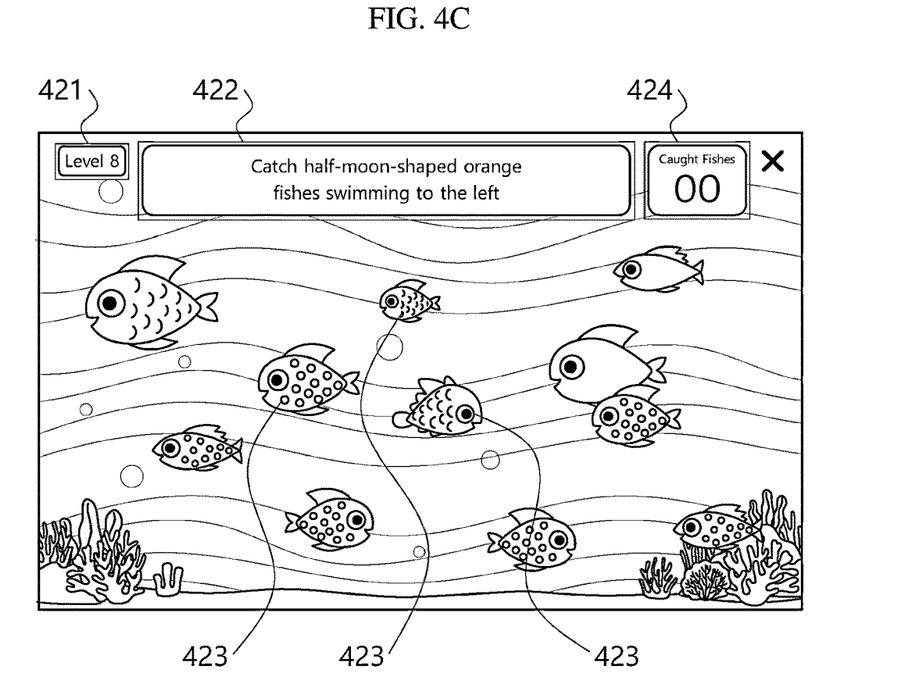
FIG. 4C is an exemplary image showing a screen of a content provided by the system for improving cognitive ability according to an embodiment.

Referring to FIG. 4C, as an example of still another form of cognitive training, the user may perform a task of checking a question by reading the phrase in a question image 422 presented as a task, and selecting an image corresponding to an answer to the question among answer images 423 displayed on the screen. In the case of the example shown in FIG. 4C, since half-moon-shaped orange fishes swimming to the left are located at the left and center of an upper part of the screen, the task may be achieved by selecting the remaining fish except for them. At this time, the number of fishes selected by the user may be displayed through a counter image 424. Also, like the content screen illustrated in FIG. 4A, in the case of this content, a level image 421 indicating the difficulty of the task may be further displayed on the screen.

Figure 4D:
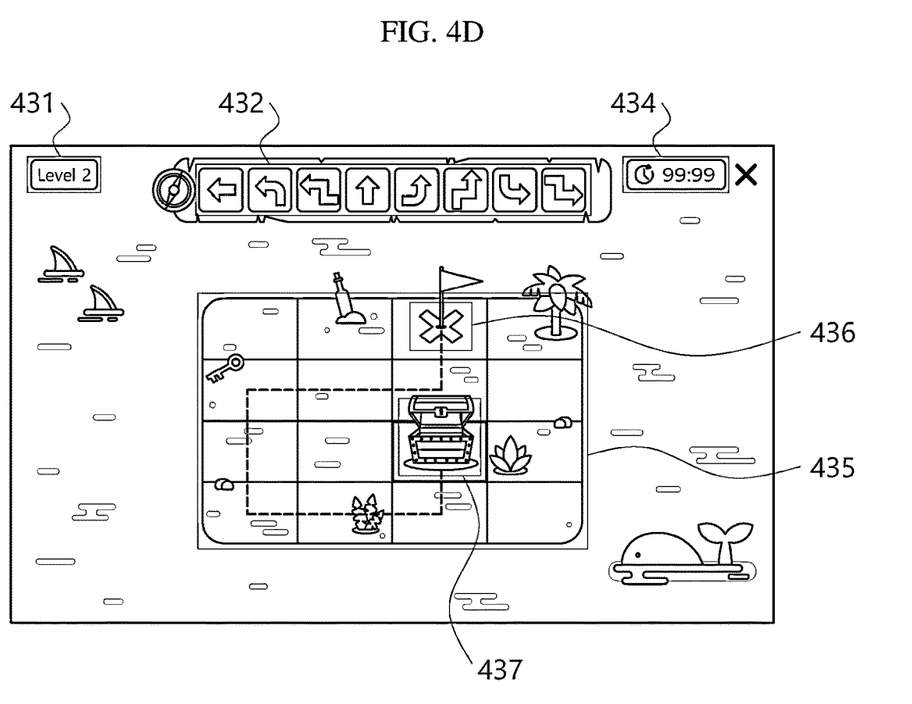
FIG. 4D is an exemplary image showing a screen of a content provided by the system for improving cognitive ability according to an embodiment.

Referring to FIG. 4D, as an example of still another form of cognitive training, the user may perform a task of seeing a series of arrows presented in an question image 432 and moving the position from a start point 436 in an answer presentation space 435 based on the arrows to reach a point 437 where a treasury corresponding to a correct answer is located. In this case, the position movement according to the selection of the user may be displayed to be recognized by the user using a dotted line as shown in FIG. 4D, a virtual character, a pointer, or the like. Like the content screen illustrated in FIG. 4A, in the case of this content, a level image 431 indicating the difficulty of a task and/or a timer image 434 indicating a consumed time may be further displayed on the screen.

Figure 4E:
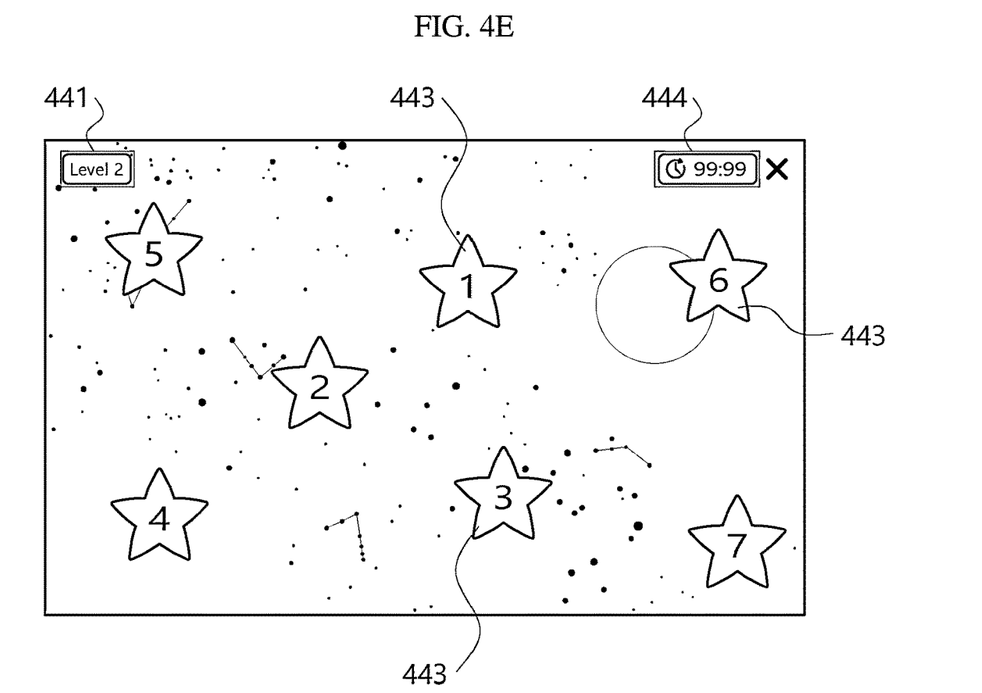
FIG. 4E is an exemplary image showing a screen of a content provided by the system for improving cognitive ability according to an embodiment.

Referring to FIG. 4E, as an example of still another form of cognitive training, the user may perform a task of seeing a plurality of question images 443 displayed with a predetermined number and selecting question images 443 displayed on the screen in an order from a small number to a large number (or, vice versa). Like the content screen illustrated in FIG. 4A, in the case of this content, a level image 441 indicating the difficulty of a task and/or a timer image 444 indicating a consumed time may be further displayed on the screen.

Figure 4F:
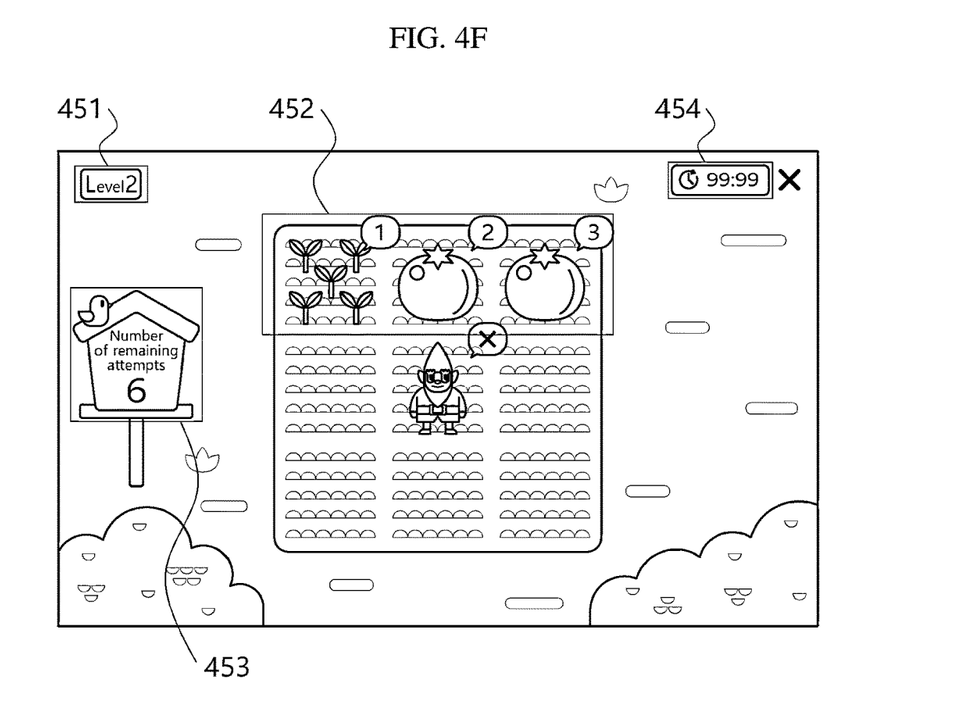
FIG. 4F is an exemplary image showing a screen of a content provided by the system for improving cognitive ability according to an embodiment.

Referring to FIG. 4F, as an example of still another form of cognitive training, the user may perform a task of selecting objects in an order according to time by looking at the objects presented in a question image 452. For example, in the case of the example shown in FIG. 4F, after tomato sprouts grow and tomato grows, and then if the tomato matures, its color becomes red. Therefore, a correct answer is to select the objects presented in the question image 452 in the order from left to right. At this time, the content may be configured so that the user may try to solve the task only a limited number of times, and in this case, the number of times the user has attempted to solve the task (or, the number of remaining attempts) may be displayed on the screen by a counter image 453. Also, like the content screen illustrated in FIG. 4A, in the case of this content, a level image 451 indicating the difficulty of a task and/or a timer image 454 indicating a consumed time may be further displayed on the screen.

The system for improving cognitive ability according to an embodiment may determine a recognition score of the cognitive training area based on the difficulty (i.e., level) achieved by the user for the cognitive training content as exemplified with reference to FIGS. 4A to 4F or the time consumed by the user in achieving the task. In addition, the score of each area of vascular disease management, exercise, nutrition management and motivation enhancement except for the cognitive training among the five cognitive areas may be determined as follows.

First, the recognition score of the vascular disease management area may be determined based on an answer of the user obtained by providing the user with medication guidance and management, education on vascular risk disease, etc. and then presenting a question related to the education content. Alternatively, the recognition score of the vascular disease management area may be determined based on the presence or absence of diabetes, hypertension, dyslipidemia, obesity, excessive drinking, and smoking, which are representative risk factors. For example, through the content, a question for checking whether the user corresponds to some of the above risk factors may be presented, and the recognition score of the vascular disease management area may be determined through an answer of the user thereto. For example, if the user has more risk factors, a lower recognition score will be given.

Next, the recognition score in the exercise field may be determined based on a participation rate of the user in physical activity. The physical activity is an institution-led activity that is periodically implemented by an operator of the system for improving cognitive ability, and a recognition score may be determined based on the number of attendance of the user. In this case, the institution-led physical activity may have differentiated forms such as a low-physical group, a general physical group, a muscular strength-enhancing type, and an aerobic-enhancing type according to a physical level of an individual. However, this is an example, and if it is impossible for the user to participate in an institution-led activity, the user may be encouraged to engage in physical activity on his/her own, and the frequency and duration of physical activity may be checked through a questionnaire, and a recognition score may be determined based thereon.

Next, the recognition score in the nutrition field may be determined based on dietary formula taken by the user. For example, through the system for improving cognitive ability, the user may be induced to have a balanced intake of vegetables, fish, nuts, fruits, olive oil, whole grains, etc. and may be induced to reduce the intake amount of alcoholic beverages, monosaccharides, fried foods, cheese, butter, and processed foods that are not good for the body. Next, a questionnaire is presented to the user through the cognitive ability improving content to check the nutrition consumed by the user, and the recognition score of the nutrition field may be determined through an answer of user thereto. Alternatively, through the cognitive ability improving content, the user may upload a picture of his/her dietary formula to the system for improving cognitive ability, and the system for improving cognitive ability may recognize objects on the picture through image processing techniques to determine the type of nutrition sources included in the dietary formula taken by the user, and the recognition score of the user in the nutrition field may be determined based thereon.

Next, the recognition score in the motivation enhancement field may be determined by suggest a video content or the like to be watched by the user participating in a cognitive ability development program or a person related to the user (e.g., a guardian such as a family member), and the recognition score in the motivation enhancement field may be determined based whether the corresponding content is completely watched, a ratio of a completely watched time among the total playback time, and/or a ratio of a watched content among the total contents when there are a plurality of contents. Alternatively, in another embodiment, the system for improving cognitive ability may allow the user to select his/her motivational state through the content and determine a recognition score based on the self-evaluation of the user. For example, the user may be allowed to watch a support video of family members through the content, and after watching the support video, the user may determine a recognition score in the motivation enhancement field based on the self-evaluated motivation state.

As described above, the system for improving cognitive ability according to an embodiment may classify the cognitive area for improving cognitive ability into five areas of vascular disease management, cognitive training, exercise, nutrition management and motivation enhancement, and derive a recognition score of the user for each area based on the content.

Figure 5:
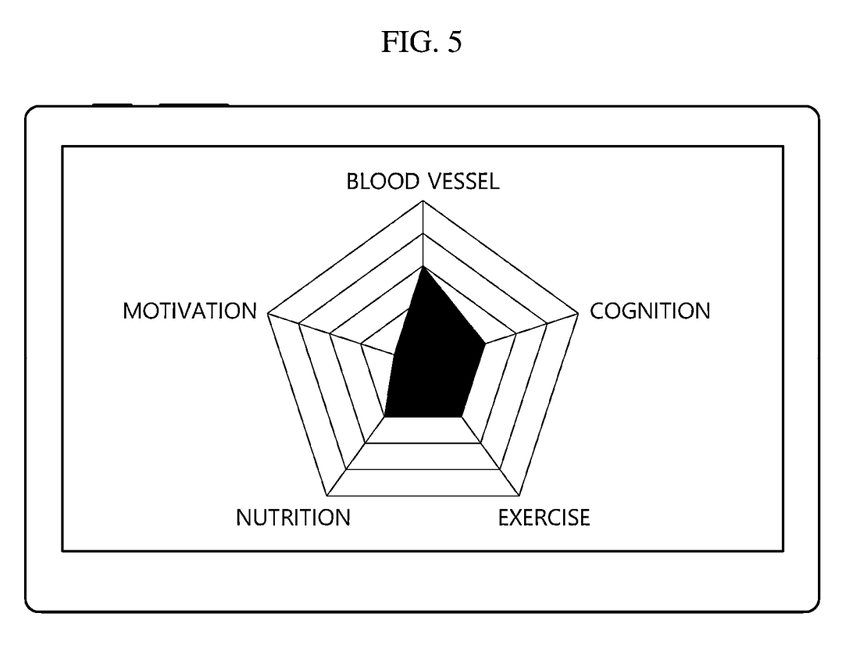
FIG. 5 is an exemplary graph showing a recognition score output on a user device by the system for improving cognitive ability according to an embodiment.

FIG. 5 is an exemplary graph showing a recognition score output on a user device by the system for improving cognitive ability according to an embodiment.

Referring to FIG. 5, the system for improving cognitive ability according to an embodiment may classify the learning of the user through the content into five cognitive areas of vascular disease management, cognitive training, exercise, nutrition management and motivation enhancement, and express cognitive ability of the user as a pentagonal graph in each area based on the recognition score achieved by the user for the content. However, this is an example, and the type and number of cognitive areas classified by the system for improving cognitive ability according to embodiments, or the method of expressing the recognition score of each area, is not limited to the form described in this specification.

Referring to FIG. 3 again, the system for improving cognitive ability according to embodiments of the present disclosure may calculate performance information of the user for the content by further using a progress rate, a user history, a participation rate, or the like in addition to the recognition score of each cognitive area calculated as described above.

In this specification, the progress rate refers to an achievement rate of the user for tasks provided in the entire content based on multi-area intervention. For example, the cognitive ability improving content includes a total of 25 tasks, 5 tasks for five cognitive areas of vascular disease management, cognitive training, exercise, nutrition management and motivation enhancement, and if the user performs 5 tasks among these tasks, the progress rate may be defined as 20%. However, this is an example, and in another embodiment, the progress rate may be defined for each cognitive area.

In still another embodiment, the progress rate may be determined as the sum of recognition scores achieved for tasks, rather than the number of tasks achieved. For example, in the above example, if the total sum of recognition scores achievable by the user for 25 tasks is 2,500 points and an average recognition score of the user achieved for 5 tasks is 80 points, the progress rate may be defined as a value obtained by dividing [the sum of scores achieved by the user] by [the sum of scores achievable for the tasks], which is 80/2,500, namely 3.2%.

In an embodiment, the user history refers to information that allows to identify a consumption type of the user about indicating which content is consumed by the user among the contents for multi-area intervention. For example, the user history may include information such as a content search history of the user, time consumed by the user on each content, the total sum of time consumed by the user on contents in a specific cognitive area, and the like.

In an embodiment, the participation rate may be information indicating how much the user actually participates in content learning intended to be repeated for a predetermined period. For example, the system for improving cognitive ability according to embodiments may be implemented as an institution type, which is used by a user who visits a hospital or a clinic, or may be implemented as a home type, which may be accessed and used by the user through a network at home. In this case, the participation rate may refer to the number of learning (or, the number of learning days) in which the user actually performs learning, from the number of available learnings for a certain period (e.g., one month).

In addition, in another embodiment, the participation rate may be defined as information on the number of days that the user continuously performs learning through the content. For example, the number of times the user has observed a predetermined learning schedule without omission may be defined as the participation rate, but is not limited thereto.

In an embodiment, in determining the customized content from the learning data of the user, log information of the screen corresponding to the content provided to the user may be further used. In this specification, the log information of the screen means calculating the time during which the user stays on each screen displayed corresponding to the content, calculating the time required for switching screens, or detecting a trajectory of an operation made using a user input means (e.g., a mouse) in each screen. For example, by tracing the trajectory of a pointer manipulation of the user using the mouse on the content screen, the position of the point on the screen where the pointer has stayed for a long time may be analyzed using the screen log, or the time during which the user has stayed on the screen may be analyzed using the log to calculate actual participation information of the user. This participation information may be used in place of or as a supplement to the participation rate described above.

The system for improving cognitive ability according to embodiments may derive the recognition score, the progress rate, the user history participation rate, the screen log information, or the like derived from the learning data through the above process as performance information of the user. In addition, the system for improving cognitive ability may determine the type of the user by analyzing the performance information of the user based on the learning result of machine learning, determine a customized content suitable for improving the cognitive ability of the user, and present the customized content to the user.

For example, the learning result using the training data set may mean that users are clustered into a plurality of groups according to performance information and, for each group, the characteristics of a content suitable for improving the cognitive ability of users of the corresponding group are matched. For example, based on the results of comprehensive analysis of the recognition score, the progress rate, the participation rate, the user history and the screen log of the users in the training data set, the performance information of the users may be displayed in the form of a data record, which is a five-dimensional value representing the performance of each of five cognitive areas including vascular disease management, cognitive training, exercise, nutrition management and motivation enhancement.

Each learning data included in the training data set is respectively expressed in the form of a five-dimensional data record, and the data record corresponding to a center point of each group (i.e., cluster) may be determined by clustering the learning data. In this case, the cognitive ability improving content may have characteristic information defining a field that can be improved through the corresponding content among five cognitive areas of vascular disease management, cognitive training, exercise, nutrition management and motivation enhancement. The characteristic information may be set by an expert in advance, and since a plurality of areas may be sometimes reinforced through one content, the cognitive ability improving contents may also be expressed in the form of 5-dimensional data record having a characteristic value for each of the five areas.

That is, in this embodiment, the learning result by machine learning may include five-dimensional data corresponding to a center data record of each data group generated by clustering the user learning data of the training data set, and a five-dimensional characteristic value of the cognitive ability improving content set as being suitable for improving cognitive ability of each data group.

At this time, if learning data is received from the target user, the system for improving cognitive ability may determine a data group to which the performance information of the target user corresponds based on the learning result. That is, this means that the type of user is determined based on the performance information of the user. The type of user may be determined by calculating distances between the data records corresponding to the center point of each data group and the performance information of the user in a five-dimensional data space having five coordinate axes corresponding to each cognitive area and then determining a data group in which the closest data record is the center point among them. Next, the cognitive ability improving content determined for the corresponding data group may be determined as the customized content of the corresponding user.

In still another embodiment, determining the type of user does not necessarily mean determining that the performance information of the user belongs to any one data group, and the customized content of the corresponding user may also be determined by calculating the similarity of the performance information of the user for each of the plurality of data groups and merging the customized content corresponding to each data group based on the similarity.

That is, in the five-dimensional data space having five coordinate axes corresponding to each cognitive area, the distances between the data records corresponding to the center point of each data group and the performance information of the user has a five-dimensional data form like (a, b, c, d, e). For example, a denotes a 5-dimensional distance between the center point of the first data group and the performance information of the user, and b denotes a 5-dimensional distance between the center point of the second data group and the performance information of the user. At this time, if the customized contents corresponding to the first to fifth data groups are referred to as A, B, C, D and E, respectively, the customized content of the user may be newly determined by defining ratios of the contents so that a customized content corresponding to each data group is included at a higher rate as the distance from the performance information of the user to the center point of the corresponding data group is shorter, and then merging the contents based on the ratios.

For example, in the above example, the distance between the center point of each data group and the performance information of the user is (a, b, c, d, e), and the merging ratio of the customized contents A, B, C, D, E in the newly generated content may be determined in proportion to the reciprocal of the distance as (1/a, 1/b, 1/c, 1/d, 1/e). At this time, merging the contents means that some of the plurality of tasks included in each content are merged with a task included in other content as described above with reference to FIGS. 4A to 4F to generate a new content in which tasks of different contents are merged.

Alternatively, the machine learning module of the system for improving cognitive ability may also perform learning on the machine learning-based analyzing model by using the performance information of the user as an input value for the machine learning-based analyzing model, and determine the type of content suitable for the user by classifying a characteristic value of a 5-dimensional vector of the learning result to correspond to a specific task or a content in which specific tasks are merged.

For the classification, the machine learning module may perform learning for the analyzing model by receiving learning data including the characteristics of content (type of task, etc.) known to be effective for users whose performance information has a constant characteristic value (e.g., the size of five-dimensional data, the value of each data item, the average of values of each data item, the standard deviation of values of each data item, etc.), and classify a content corresponding to performance information of an unknown user to be analyzed based on a parameter determined in the learning result. At this time, as an input value to the analyzing model, 5-dimensional data itself, which is the performance information of the user, may be used, or a 5-dimensional vector (a, b, c, d, e) indicating the distance between the center point of each data group obtained by clustering as described above and the performance information of the user or a five-dimensional vector (1/a, 1/b, 1/c, 1/d, 1/e) representing the reciprocal of the distance may be used.

However, the method for determining a user customized content described above is exemplary, and the method for determining a customized content from the learning data of the user based on machine learning by the system for improving cognitive ability according to embodiments is limited to the above example.

Meanwhile, the operation by the method for improving cognitive ability according to embodiments as described above may be at least partially implemented as a computer program and recorded in a computer-readable recording medium. The computer-readable recording medium in which the program for implementing the operation of the method for improving cognitive ability according to embodiments is recorded includes all kinds of recording devices in which computer-readable data is stored. Examples of the computer-readable recording medium include ROM, RAM, CD-ROM, magnetic tape, floppy disk, and optical data storage. In addition, the computer-readable recording medium may be distributed in computer systems connected through a network, and computer-readable codes may be stored and executed in a distributed manner. In addition, functional programs, codes, and code segments for implementing this embodiment will be easily understood by those skilled in the art to which this embodiment belongs.

Although the present disclosure has been described above with reference to the embodiments shown in the drawings, it will be understood by those skilled in the art that this is merely an example, and that various modifications and variations can be made therefrom. However, such modifications should be considered as falling within the technical protection scope of the present disclosure. Therefore, the true technical protection scope of the present disclosure should be determined by the technical idea of the appended claims.

Embodiments relate to a technology associated with a system for improving cognitive ability, which performs a customized dementia prevention function by reflecting individual characteristics through a comprehensive program including multi-area intervention important for dementia prevention and may be used by multiple users since it may be implemented not only in an institutional type where the system is used by a user visiting an institution and but also in an at-home type where the system is used at home.

The invention claimed is:

1. A system for improving cognitive ability by using a machine learning, comprising:
    a processor and a memory device communicatively coupled to the processor, and the memory device stores instructions operable when executed by the processor to cause:
    an input processor to receive a training data set, wherein the training data set includes a plurality of cognitive areas of vascular disease management, cognitive training, exercise, nutrition management, and motivation enhancement in a form of a five-dimensional data record;
    a data labeling processor of the input processor to label the training data set by using a customized content information and provide the labeled training data to a machine learning processor;
    the machine learning processor to perform the machine learning with the labeled training data and to store a learning result of the machine learning;
    a content providing processor to provide a cognitive ability improving content to a user;
    the input processor to receive a user learning data of the user for the cognitive ability improving content;
    an analyzing processor to extract performance information of each of a plurality of cognitive areas based on the user learning data; and
    a machine learning processor to determine a characteristic of a next cognitive ability improving content to be provided to the user by using the performance information of each of the plurality of cognitive areas and the stored learning result,
    wherein the learning result comprises five-dimensional data corresponding to a center data record of each data group generated by clustering the user learning data of the training data set, and a five-dimensional characteristic value of the cognitive ability improving content set as being suitable for improving cognitive ability of each data group,
    wherein the plurality of cognitive areas consists of the vascular disease management, the cognitive training, the exercise, the nutrition management, and the motivation enhancement,
    wherein the performance information is determined in the form of a data record, which is a five-dimensional value representing a performance of each of five cognitive areas including the vascular disease management, the cognitive training, the exercise, the nutrition management and the motivation enhancement, based on results of comprehensive analysis of a recognition score, a progress rate, a participation rate, a user history and a screen log of users in the training data set,
    wherein, each user learning data included in the training data set is respectively expressed in the form of the five-dimensional data record,
    wherein, the cognitive ability improving content comprises characteristic information defining a field that is improved through the corresponding content among the five cognitive areas, and
    wherein the user history includes at least one of a content search history of the user, time consumed by the user on each content, a total sum of time consumed by the user on contents in a specific cognitive area.

2. The system for improving cognitive ability according to claim 1,
    wherein the memory device stores instructions operable when executed by the processor to cause the analyzing processor to determine the performance information based on a consumed time of each of the plurality of cognitive areas.

3. The system for improving cognitive ability according to claim 2,
    wherein the memory device stores instructions operable when executed by the processor to cause:
    the input processor to receive personal information of the user; and
    the analyzing processor to determine a reference value for deriving the performance information from at least one of the recognition score, the consumed time, the progress rate and the participation rate by using the personal information of the user.

4. The system for improving cognitive ability according to claim 1,
    wherein the machine learning processor includes:
    a machine learning model learning processor; and
    a machine learning model determining processor,
    wherein the memory device stores instructions operable when executed by the processor to cause:
    the machine learning model learning processor to generate the learning result by performing machine learning using the training data set; and
    the machine learning model determining processor to determine a characteristic of the cognitive ability improving content corresponding to the performance information of each of the plurality of cognitive areas by using the learning result.

5. A method for improving cognitive ability by using a machine learning, wherein a processor and one or more memory devices communicatively coupled to the processor, and the one or more memory devices stores instructions operable when executed by the processor to perform:
    receiving a training data set, wherein the training data set includes a plurality of cognitive areas of vascular disease management, cognitive training, exercise, nutrition management, and motivation enhancement in a form of a five-dimensional data record;
    labeling the training data set by using a customized content information and provide the labeled training data for the machine learning;
    performing the machine learning with the labeled training data;
    storing a learning result of the machine learning;
    providing a cognitive ability improving content to a user for improving cognitive ability;
    receiving a user learning data of the user for the cognitive ability improving content;
    extracting performance information of each of a plurality of cognitive areas based on the user learning data; and determining a characteristic of a next cognitive ability improving content to be provided to the user by using the performance information of each of the plurality of cognitive areas and the stored learning result of the machine learning, wherein the learning result comprises five-dimensional data corresponding to a center data record of each data group generated by clustering the user learning data of the training data set, and a five-dimensional characteristic value of the cognitive ability improving content set as being suitable for improving cognitive ability of each data group, wherein the plurality of cognitive areas consists of the vascular disease management, the cognitive training, the exercise, the nutrition management, and the motivation enhancement, wherein the performance information is determined in the form of a data record, which is a five-dimensional value representing a performance of each of five cognitive areas including the vascular disease management, the cognitive training, the exercise, the nutrition management and the motivation enhancement, based on results of comprehensive analysis of a recognition score, a progress rate, a participation rate, a user history and a screen log of users in the training data set, wherein, each user learning data included in the training data set is respectively expressed in the form of the five-dimensional data record, wherein, the cognitive ability improving content comprises characteristic information defining a field that is improved through the corresponding content among the five cognitive areas, and wherein the user history includes at least one of a content search history of the user, time consumed by the user on each content, a total sum of time consumed by the user on contents in a specific cognitive area.

6. The method for improving cognitive ability according to claim 5,
wherein the step of generating a learning result includes:
receiving the training data set; and
labeling the training data set by using a customized content preset for data included in the training data set.

7. The method for improving cognitive ability according to claim 5,
wherein the step of extracting performance information includes:
determining the performance information based on at least one of a recognition score of each of the plurality of cognitive areas, a consumed time of each of the plurality of cognitive areas, a progress rate of each of the plurality of cognitive areas and a participation rate of each of the plurality of cognitive areas.

8. The method for improving cognitive ability according to claim 7, before the step of extracting performance information, further comprising:
receiving personal information of the user; and
determining a reference value for deriving the performance information from at least one of the recognition score, the consumed time, the progress rate and the participation rate by using the personal information of the user.

9. A non-transitory computer readable recording medium including executable instructions, wherein the instructions, when executed by a processor, cause the processor to perform:
receiving a training data set, wherein the training data set includes a plurality of cognitive areas of vascular disease management, cognitive training, exercise, nutrition management, and motivation enhancement in a form of a five-dimensional data record;
labeling the training data set by using a customized content information and provide the labeled training data for the machine learning;
performing the machine learning with the labeled training data;
storing a learning result of the machine learning;
providing a cognitive ability improving content to a user;
receiving a user learning data of the user for the cognitive ability improving content;
extracting performance information of each of a plurality of cognitive areas based on the user learning data; and
determining a characteristic of a next cognitive ability improving content to be provided to the user by using the performance information of each of the plurality of cognitive areas and the stored learning result of the machine learning, wherein the learning result comprises five-dimensional data corresponding to a center data record of each data group generated by clustering the user learning data of the training data set, and a five-dimensional characteristic value of the cognitive ability improving content set as being suitable for improving cognitive ability of each data group, wherein the plurality of cognitive areas consists of the vascular disease management, the cognitive training, the exercise, the nutrition management, and the motivation enhancement, wherein the performance information is determined in the form of a data record, which is a five-dimensional value representing a performance of each of five cognitive areas including the vascular disease management, the cognitive training, the exercise, the nutrition management and the motivation enhancement, based on results of comprehensive analysis of a recognition score, a progress rate, a participation rate, a user history and a screen log of users in the training data set, wherein, each user learning data included in the training data set is respectively expressed in the form of the five-dimensional data record, wherein, the cognitive ability improving content comprises characteristic information defining a field that is improved through the corresponding content among the five cognitive areas, and wherein the user history includes at least one of a content search history of the user, time consumed by the user on each content, a total sum of time consumed by the user on contents in a specific cognitive area.

* * * * *